United States Patent [19]
Lo

[11] Patent Number: 5,576,626
[45] Date of Patent: Nov. 19, 1996

[54] COMPACT AND LOW FUEL CONSUMPTION FLAME IONIZATION DETECTOR WITH FLAME TIP ON DIFFUSER

[75] Inventor: Chi K. Lo, Fremont, Calif.

[73] Assignee: Microsensor Technology, Inc., Fremont, Calif.

[21] Appl. No.: 375,330

[22] Filed: Jan. 17, 1995

[51] Int. Cl.⁶ .................................................. G01N 27/62
[52] U.S. Cl. ........................ 324/464; 436/154; 324/468
[58] Field of Search ............................... 324/464, 468; 422/54; 436/154; 73/23.4, 23.35

[56] References Cited

U.S. PATENT DOCUMENTS

| | | | |
|---|---|---|---|
| 3,545,936 | 12/1970 | Jentzsch et al. | 422/54 |
| 4,182,740 | 1/1980 | Hartmann et al. | 436/154 |
| 5,073,753 | 12/1991 | Collings et al. | 324/468 |
| 5,180,983 | 1/1993 | Murata et al. | 324/464 |

FOREIGN PATENT DOCUMENTS

| | | | |
|---|---|---|---|
| 2430009 | 2/1980 | France | 324/468 |
| 0783676 | 11/1980 | U.S.S.R. | 324/468 |

OTHER PUBLICATIONS

F. W. Karasek et al., "Basic Gas Chromatography–Mass Spectrometry, Principles and Techniques," University of Waterloo, Waterloo, Ontario, Canada, Dec. 1988, pp. 16–21 and 25–35.

Author Unknown, "Analytical Chemistry," vol. 41, No. 2, Feb. 1969, pp. 304–305.

Matthew J. O. Brien, "Detectors in Modern Practice of Gas Chromatography," Robert L. Grob, John Wiley & Sons, Dec. 1985, pp. 241–245.

*Primary Examiner*—Maura K. Regan
*Attorney, Agent, or Firm*—Skjerven, Morrill, MacPherson, Franklin & Friel; Norman R. Klivans

[57] ABSTRACT

A compact and low fuel consumption flame ionization detector includes a precisely pored metallic disk or a silicon micro-machined diffuser plate through which the sample gas tube extends a minimum distance (less than 2 mm). The oxidant flows into the detector in a direction parallel to a plane of the diffuser plate, passes into a small cavity under the diffuser, and then passes through a large number of very small holes formed in the diffuser plate before encountering the sample gas flow at the end of the gas tube. A narrow diameter collector is closely spaced to the end of the gas tube. The direction of feeding the air and the diffuser plate (which acts as a baffle) provide laminar flow and eliminate the flicker noise which would otherwise occur due to the air flow inlet being located very close to the gas tube end. The FID is vertically compact and operates at a high electric field strength, exceeding 90 V/mm. The FID has a low fuel flow, typically 12–15 ml/min and therefore a low oxidant flow rate, typically 120–150 ml/min, advantageous to the operation of a portable gas chromatograph. The compactness of the FID also requires less electrical power to heat the detector to operating temperature, thus prolonging battery life.

14 Claims, 3 Drawing Sheets

COMPACT AND LOW FUEL CONSUMPTION FLAME IONIZATION DETECTOR WITH FLAME TIP ON DIFFUSER

BACKGROUND OF THE INVENTION

1. Field of the Invention

This invention relates to flame ionization detectors for e.g. gas chromatography and more particularly to such detectors of compact size and low fuel requirement.

2. Description Of The Prior Art

One type of detector used in gas chromatography is called a flame ionization detector (FID). The effluent gas (sample) from the analytical column of a gas chromatograph is premixed with hydrogen makeup gas and burned at the top of a flame tip with air (or oxygen) as oxidant. The burning decomposes the organic analytes and ionizes them quantitatively. The resulting ions or electrons are collected by a cylindrical electrode located adjacent the flame tip. Another electrode located below the flame tip provides a bias potential, so that an electrical field develops between the two electrodes. Current flowing between the two electrodes is proportional to the number of ions or electrons produced and collected.

In a flame ionization detector, a diffusion flame is the most efficient way to ionize the analyte (sample). The introduction of air must also be done very smoothly to minimize flicker noise, caused by having a flame burning unsteadily, and typically resulting from an air inlet that does not bring the air to the flame tip smoothly. It is known (see *Modern Practice of Gas Chromatagraphy*, ed. Robert L. Grob, 1985, p. 244) to introduce the air through a porous diffuser located well below the tip of the jet. Flicker noise is also reduced in the prior art by allowing sufficient vertical distance between the air inlet and the flame tip so as to develop a laminar air flow, however a sufficient vertical distance undesirably results in a physically longer detector.

Conventional flame ionization detectors tend to use a high flow rate of e.g. hydrogen make-up gas (greater than 30 ml./min), thus requiring a correspondingly high air flow rate for the burning process. For portable gas chromatographs, this requires frequent recharge of the hydrogen and air cylinders, which is undesirable. Also, the high flow rate of hydrogen creates a longer and wider flame, requiring a correspondingly physically large collector, hence increasing overall detector size.

A prior art flame ionization detector shown in FIG. 1 includes signal probe 10, igniter probe 12, flame tip assembly 14, spring clip 16 (which is the first electrode), igniter coil 18, insulator 20, and a collector tube (second electrode) 22. (No air diffuser is present in this detector). The flame is created by burning hydrogen plus the analyte in air or oxygen. A bias potential of up to 300 V is maintained between spring clip 16 and collector tube 22. Ions or electrons formed during the combustion process are collected by collector tube 22 and result in the flow of a small electrical current, which is measured by an external circuit. The hydrogen flame by itself produces very few ions or electrons, i.e. very low electrical current, but when an organic compound (e.g. a hydrocarbon) is present in the gas stream in the form of a gas chromatograph peak, large quantities of ions and electrons proportional to the number of organic molecules are created. During combustion of an organic compound, both ions and electrons are formed. Depending on the polarity of the electrodes, either ions or electrons are collected. If the bias electrode (the spring clip of FIG. 1) is negative and the collector tube is positive, electrons will be collected. When the bias electrode is positive and the collector tube is negative or grounded, ions are collected. Ions are usually easier to collect because of their larger size. An elevated current is produced and can be recorded (observed) by an external circuit. A recording of the current versus time reproduces the mass of organic compounds in the gas chromatograph peak.

In addition to requiring relatively high gas flow rates, the prior art detector of FIG. 1 is disadvantageously large, typically having a height H of about 5 to 7 cm. This is because a large distance must be allowed to smooth the inlet air flow in order to reduce the flicker noise caused by the air flow turbulence. The distance h, which is from the air inlet to the top of the flame tip, for this prior art detector is about 2 to 2.5 cms.

Additionally, the flame ionization detector of FIG. 1 is assembled from a number of individually fabricated metal and ceramic components each of which is relatively large. Collector tube 22 is an example. Its height is greater than h, the distance between the air inlet and the top of flame tip. Probes 10 and 12 are also bulky, resulting in an undesirably large horizontal dimension. The large size of this flame ionization detector makes it difficult to use in portable applications.

Flame tip inside diameters used in prior art detectors range from 0.010 to 0.020" (0.254 to 0.508 mm). A larger flame tip requires a larger hydrogen flow to maintain an efficient ionization flame. This produces a larger flame in terms of height and radius and requires a larger collector, thus increasing the size of the detector. To build a small flame ionization detector for portable gas chromatograph, a smaller flow of hydrogen must be used and its use reduces the size of the collector and subsequently the size of the detector in addition to the advantage of having better gas economy and ease of operation (due to not needing to recharge gas cylinders so frequently).

SUMMARY

In accordance with the present invention a flame ionization detector has a very efficient diffusion flame, and requires only a low hydrogen make-up gas and air flow. Typical flow rates are 12 ml/min for hydrogen make-up gas and 120 ml/min for air. The detector response is fast, its size is small and flicker noise is minimized without needing a significant vertical distance between the air inlet and the flame tip. While the background noise of conventional flame ionization detectors is reported to be on the order of a few picoamperes, the present invention can achieve a background noise of a small fraction of a picoampere (e.g. <0.2 pA) even under a high electrical field strength of e.g. 220 V/mm. (See "The flame ionization detector" in *Detectors for Capillary Chromatography* edited by H. H. Hill and D. G. McMinn, Wiley InterScience Pub., New York, 1992, page 14.)

A flame ionization detector in accordance with the present invention includes a small inside diameter tube for carrying the sample from the column of the gas chromatograph together with the hydrogen makeup gas. This small I.D. tube passes through a hole in a diffuser plate which includes a large number of very small and precisely formed diffuser "microchannels" formed through it. The tube terminates immediately above the upper surface of the diffuser plate, thus locating the flame tip as close as possible to the upper surface of the diffuser plate. The air (or other oxidant)

needed for combustion is introduced from beneath the diffuser plate flowing in a direction parallel to the plane defined by the diffuser plate (perpendicular to the diffuser microchannels) and flows through the diffuser microchannels to support the combustion at the flame tip assembly. The diffuser plate and the direction of air flow to the diffuser plate thereby minimize turbulence in the air flow when the air reaches the flame tip, eliminating flame flicker noise. The diffuser plate may be a porous metal plate, an etched silicon plate, or other similar structure.

This diffuser plate, which advantageously is located very near the flame tip, allows the air to be introduced immediately adjacent the flame tip, thus eliminating the need for a substantial vertical separation between the air inlet and the flame tip. This structure reduces overall detector height, allowing a more compact (portable) device. A typical distance from the flame tip to the upper surface of the diffuser plate is 1 to 2 mm. The flame tip is located at the lower end of a 4 to 6 mm height collector. The collector has an I.D. of about 4.5 mm to achieve high electrical field strength for efficient collection. This close spacing advantageously minimizes the internal volume of the detector. The overall height of the detector assembly may advantageously be less than 1.5 centimeter. The overall compactness also conserves electrical power to heat the detector to operating temperatures.

The flicker noise minimization due to turbulence reduction results in a higher signal to noise ratio and lowers the detection limit of the detector. The present device is very sensitive, and can detect a small quantity of hydrocarbons. While a typical FID is reported to respond to 20 pg of a component from a high resolution capillary column (See "Flame Ionization Detector" by Dennis G. McMinn and Herbert H. Hill, IN "Detectors for Capillary Chromatography", edited by Herbert H. Hill and Dennis G. McMinn, 1992, pg. 16.), the present device, under general operating conditions, can detect down to 0.5 pg of butane in a 500 msec fast peak. Optimizing the injection volume, gas flows and operating temperature can lower the detection limit to at least 0.25 pg of butane. Thus the present device is one to two orders more sensitive than in the prior art. Moreover, the present device can analyze very small sample volumes, down to 3.5 μl.

The diffuser plate in one version is fabricated by micromachining a silicon wafer, by etching the diffusion microchannels through the plate and also micromachining the wafer so that a thinner central portion of the plate (which includes the diffusion microchannels) is surrounded by a thicker rim for mechanical strength. In another version, the diffuser plate is a commercially available porous metal plate. The gas carrying tube in one version is metal clad fused silica. This metal cladding is one electrode, the second electrode being a conductive metal cylinder located above the flame tip area.

The flame ignition device is in one version a high voltage sparking (discharging) needle or pin resting horizontally on the top of a ceramic structure enclosing the collector. Sparking occurs when the voltage is about 1500 V and ignites the hydrogen/air mixture. The sparking gap needle or pin (pointed metal conductor) is maintained at a high voltage versus an electrically grounded surface very close to the needle. Ignition may also be by means of a hot wire. The sparking gap is easier to install and operate than the hot wire. There is no need to control the electrical current with the sparking gap.

Also in accordance with the invention, for detecting low concentrations of sample, a high electrical field strength is used. This field strength is over 150 V/mm and preferably in the range of 220 to 250 V/mm to maximize the signal to noise ratio. The small physical size allows provision of such a strong electric field with fairly modest voltages (700 to 800 V). The physically much larger prior art FIDs would require dangerously high voltages to provide such a strong electric field.

BRIEF DESCRIPTION OF THE DRAWINGS

FIGS. 2b and 2c show detail of the apparatus of FIG. 2a.

DETAILED DESCRIPTION OF THE PREFERRED EMBODIMENTS

Figure 1:
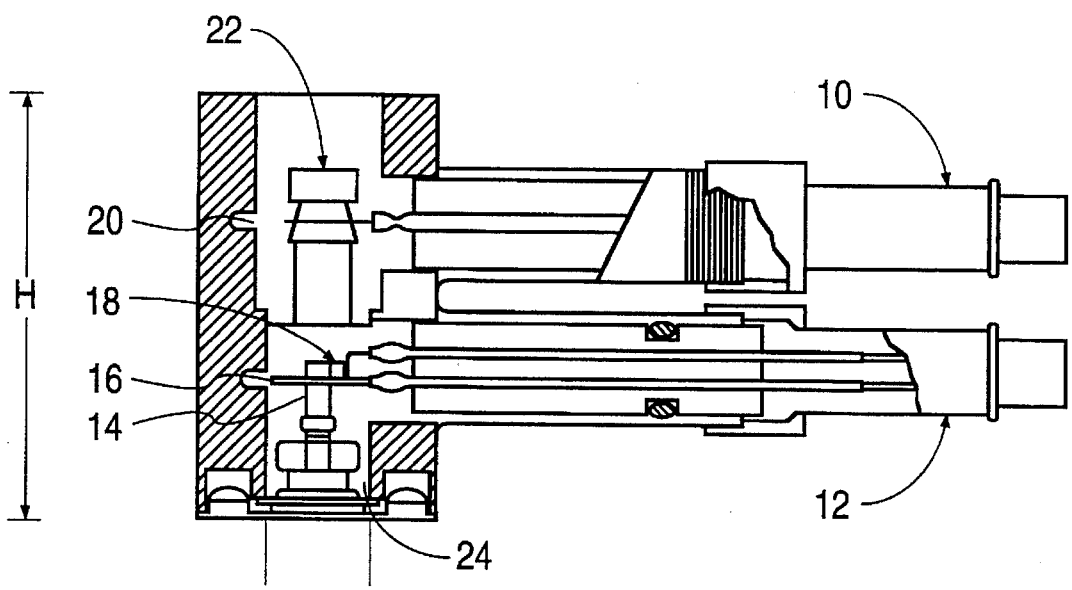
FIG. 1 shows a prior art flame ionization detector.
Figure 2A:
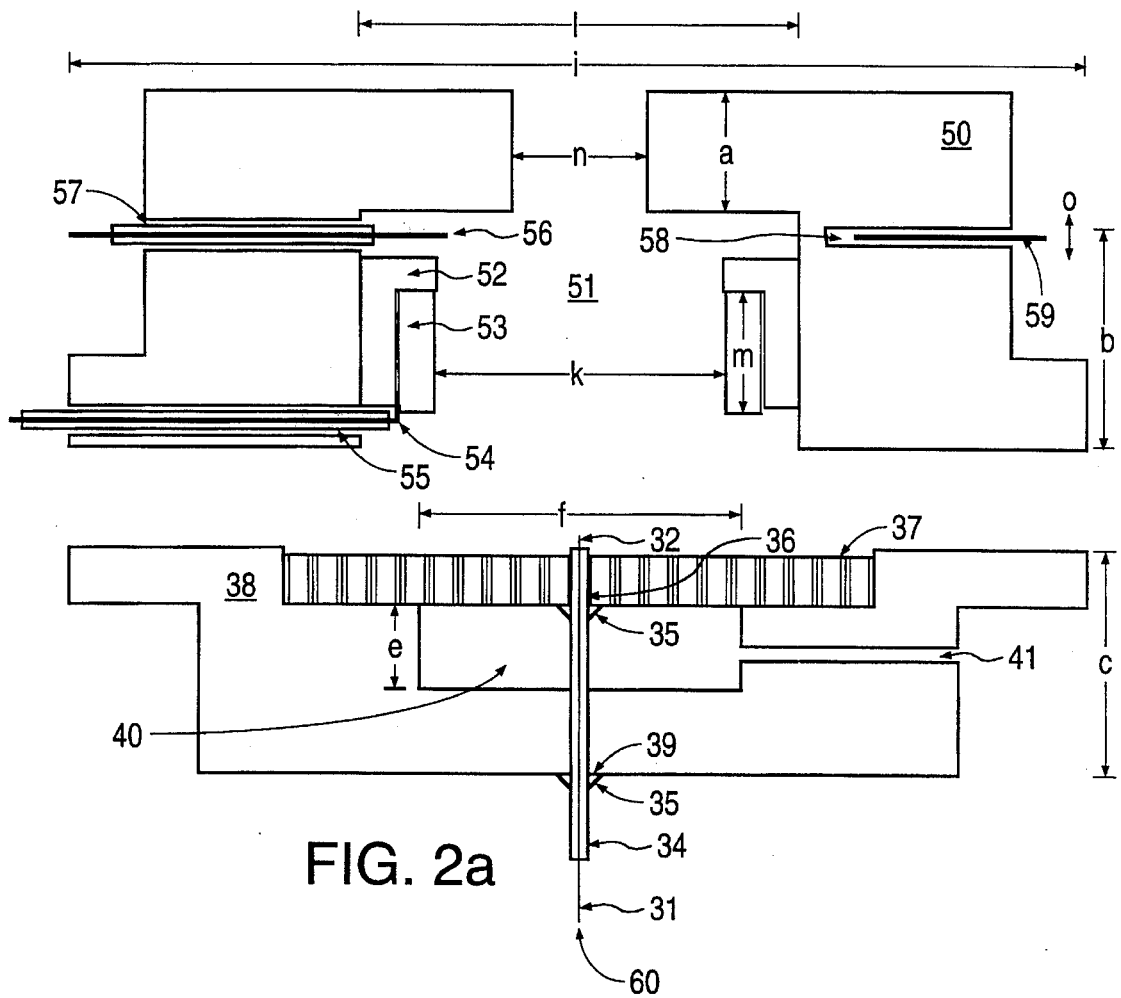
FIG. 2a shows a flame ionization detector in accordance with the present invention.

FIG. 2a (not to scale) shows in cross section a flame ionization detector (FID) in accordance with the present invention.

The flame tip 32 is the end of a length of aluminum clad fused silica capillary tube 31. The tube 31 I.D. is e.g. 100, 175 or 220 micrometers (μm). (These and other dimensions and materials herein are exemplary and not limiting.) The aluminum cladding 33 (see FIG. 2b) is 20 to 40 micrometers thick. Other metal cladding may be used or other metal may be combined with the aluminum. Such clad tubing is commercially available from Scientific Glass Engineering, part nos. 060-220, 060-175 and 060-100. The surface of fused silica is known to provide high inertness and purity for the passage of gas chromatograph analytes. Fused silica is also extremely refractory.

Figure 2B:
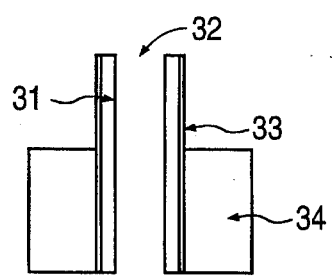

Detail of tube 31 is shown in FIG. 2b. A high bias voltage potential is provided to the aluminum cladding 33 which is the first electrode of the flame ionization detector so that the electrical field strength is e.g. up to 250 V/mm. The gas sample 60 (shown schematically in FIG. 2a), provided from the column of a conventional gas chromatograph, is conventionally premixed with make-up hydrogen (not shown) and directed to the other end of tube 31. The aluminum clad fused silica tube 31 is fixed and insulated in a ceramic tube 34. Only about 1 mm of tube 31 is exposed and that is the flame tip 32. The upper end of ceramic tube 34 is bonded with a high temperature and electrically non-conductive adhesive 35 to extend about 500 micrometers from the central hole 36 (which is about 850 micrometers in diameter) of diffuser plate 37.

The electrode bias voltage is provided by a conventional high voltage circuit that includes a standard 12 V DC primary supply that powers a high voltage power supply providing up to 1500 V for both ignition and electrode biasing. The high voltage power supply of the type commercially available is stable with low ripple. A regulatory circuit may be added to maintain a stable primary supply voltage. A switch connects the high voltage supply to alternatively the ignition circuit or the first FID electrode; the second electrode is held at ground. Other sources of high voltage may be used alternatively.

Ceramic is an extremely good electrical insulator and insulates the first electrode 33 (at the bias potential) from the rest of the structure. Diffuser plate 37 is bonded to a metal base plate 38 by a high temperature adhesive. Tube 31 and ceramic sheath tube 34 are also bonded by adhesive 35 to base plate 38 at central hole 39 which is 850 micrometers in diameter. Base plate 38 defines a central cavity 40.

Base plate 38 also defines a horizontal channel 41 which communicates with cavity 40. Channel 41 is 860 micrometers in diameter. A stainless steel air tube with a diameter of 800 micrometers (not shown) is connected to the outside end of channel 40 by means of a high temperature adhesive. Channel 41 provides air or other oxidant to the detector.

Figure 2C:
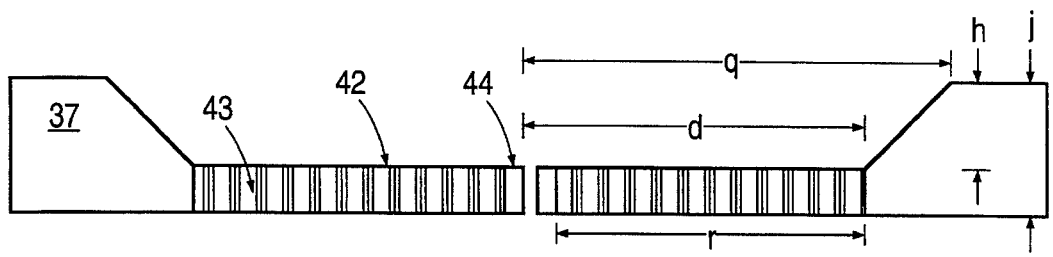

Diffuser plate 37 can be a precisely pored disk as provided by Mott Metallurgical Corporation (Part No. 1000-.500-.039-2 or 1000-.375-.039-2). These stainless steel disks have 2 micrometer diameter pores. Diffuser plate 37 (which can also be formed by silicon micromachining as described below) has central cavity 42. Detail of diffuser plate 37 is shown in FIG. 2c. Many tiny microchannels 43 in the central portion 44 of diffuser plate 37 diffuse the air from channel 41 to the combustion compartment 51. There are no diffuser holes in the very central portion 44 of diffuser plate 37; this is intended to minimize flame flickering caused by direct impact of the incoming air flow on the flame.

Base plate 38 is fastened by screws to top metal plate 50. Fastening can also be done by a high temperature adhesive. Metal plate 50 defines a large cylindrical bore in its center. The lower portion of the bore is larger and is the combustion chamber 51. A ceramic sheath 52 is inserted into combustion chamber and metal cylinder 53 is inserted into the ceramic sheath 52. Metal cylinder 53 is the second electrode (collector) of the detector. Ceramic sheath 52 insulates this second electrode 53 from the rest of the structure.

A polyimide, teflon or ceramic insulated conductor wire 54 is passed through a lateral predrilled channel at the bottom of plate 50. Wire 54 contacts electrode 53 and is a signal lead. This signal lead 54 is conventionally connected to an external current measuring circuit (not shown). A ceramic sheathed fine metal pin 56 is passed into the top portion of combustion chamber 51 through another lateral predrilled channel 57. Metal pin 56 discharges and sparks when the applied voltage is about 1500 V. The spark then ignites the flame. Another lateral channel holds a temperature sensor 59.

Dimensions for one version of the device of FIG. 2 are shown in Table 1; these dimensions (and others provided herein) again are illustrative and not limiting. Also the materials described herein are exemplary rather than limiting. It will be understood by one of ordinary skill in the art that the dimensions, materials, and elements of the structure may be modified in accordance with the spirit of the invention.

| dimension - FIG. 2 | value |
|---|---|
| a | 1000 μm |
| b | 7000 μm |
| c | 4570 μm |
| d | 3023 μm |
| e | 1500 μm |
| f | 6046 μm |
| h | 250 μm |
| i | 18,225 μm |
| j | 300 μm |
| k | 4550 μm |
| l | 8150 μm |
| m | 5000 μm |
| n | 3000 μm |
| o | 800 μm |
| q | 3300 μm |
| r | 2800 μm |

The external and internal diameter of the collector in one embodiment are 6.4 and 4.5 mm, respectively. A very small flame allows the use of a small collector, and a small collector reduces the overall size of the FID.

The flame tip is located 1–2 mm (less than 5 mm) above the diffuser surface. Using an air discharge direction that is parallel to the plane of the diffuser plate and hence perpendicular to the diffuser channels (to prevent the air flow from hitting the diffuser directly), a "turbulence buffer" like passage zone (chamber 40) is created. Together with the fine and evenly distributed diffuser channels in the diffuser plate, a very smooth flow of air out to the flame tip is achieved, minimizing the flicker noise.

Due to miniaturizing, the collector 53 is a cylinder only about 5 mm long. With its ceramic sheath 52, it is about 6 mm long. The high voltage discharge pin 56 is therefore only 6 mm away from the flame tip (source of fuel) and can easily ignite the gas mixture. Most of the discharge pin 56 (except the tip) is protected by the ceramic sheath 52 insulating the collector cylinder 53. This protection plus pin 56 being spaced away from the axial flow of the burning product minimizes residue deposit on the pin 56 surface.

It will be understood that the FID in use is assembled to form a unitary structure. The overall (vertical) height of the device in this exemplary embodiment is less than 1.50 centimeters.

The diameter of each of the microchannels in the micromachined embodiment 43 is also approximately 2 micrometers and there are approximately 17,000 microchannels provided with a center-to-center spacing of approximately 45 micrometers. The particular layout of the microchannels is not believed to be critical. The thickness of the central portion of the diffuser plate 37 which contains the microchannels 43 is approximately 50 micrometers, although this dimension is also not critical.

A typical gas flow 60 is about 12 ml/min, of which approximately 1–2 ml/min is the carrier flow containing the analyte and the remainder is the hydrogen makeup gas. Optimum fuel/flow is about 15 ml/min for a flame tip with an inside diameter of 175 μm. This gives high sensitivity. To save fuel, the fuel flow can be reduced to 10 ml/min. The air flow stream through channel 41 is approximately 10 times the flow 60, as is conventional. Higher air flow increases sensitivity slightly.

Advantageously the present invention uses a very high electrical field strength (e.g. up to 250 V/mm) to collect the ions. For the FID, there is an increased signal to noise ratio when the field strength is increased. The increase has been found to be extraordinary when the field strength is over 150 V/mm. However, while the strength of the signal is increased by the increase of field strength, detector noise is also magnified. An optimum range of about 220–250 V/mm has been found where the gain of signal to noise ratio is the maximum. No known prior art uses such a high electrical field to collect ions or electrons. Theoretically, ions are being multiplied and so a stronger signal is produced. Good linearity of the response under this bias voltage is maintained from 30 ppb to at least 10,000 ppm of sample concentration where e.g. the sample contains propane, butane and pentane.

Operating under such a high field strength makes it possible to determine low concentration (e.g. less than 0.1 ppm) of analytes. For higher concentrations, a smaller field strength is sufficient. It has been found that maintaining the diffuser plate at a potential (voltage) opposite in polarity to that of the flame tip (first electrode), including the diffuser plate being grounded, increases signal to noise ratio.

Figure 3A:
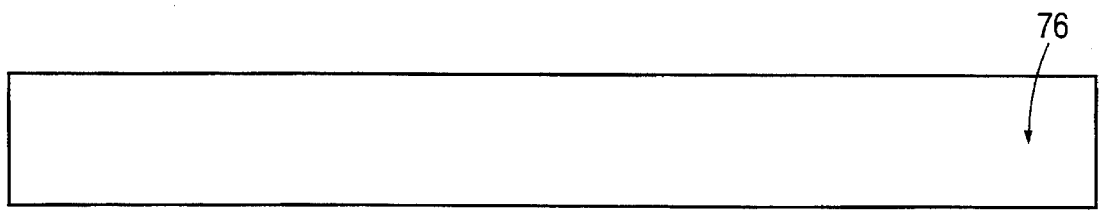
FIGS. 3 a to 3d show fabrication of a micromachine diffuser plate in accordance with the present invention.

FIGS. 3a through 3d show fabrication by silicon processing techniques of a silicon diffuser plate in accordance with one embodiment of the invention. FIG. 3a begins with a conventional silicon wafer 76 (substrate) of 300 micrometer thickness. It is to be understood that these figures show only a portion of the wafer and that a number of such diffuser plates (each having a size of about 1 cm by 1 cm) would be formed simultaneously in one wafer and then the individual diffuser plates are conventionally scribed and separated into individual components.

Figure 3B:
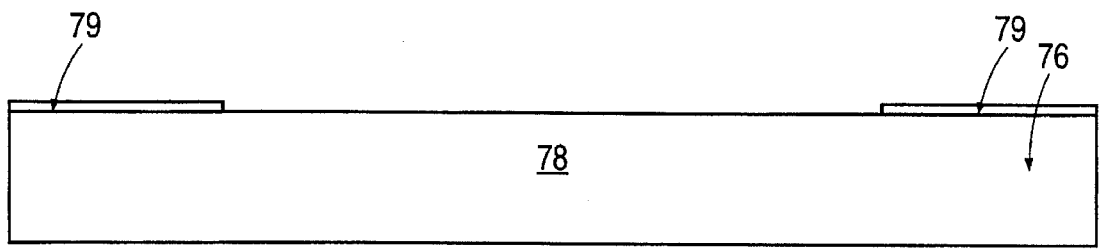
Figure 3C:
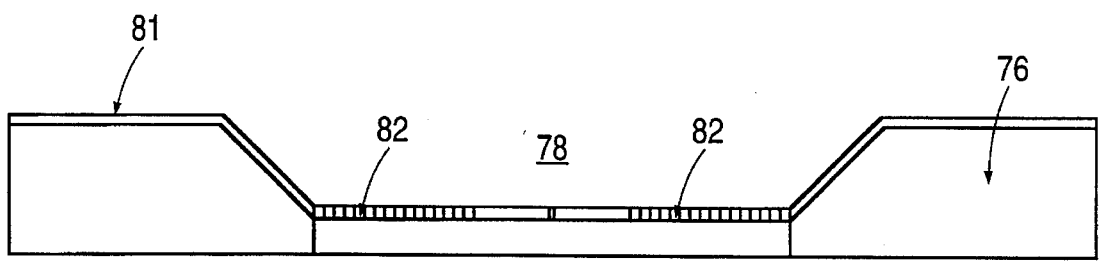

Next in FIG. 3b, a central portion 78 of substrate 76 is conventionally exposed by a patterned photoresist mask layer 79 and etched using an anisotropic etch defining cavity 78 in FIG. 3c. Mask layer 79 is then stripped. Then in FIG. 3c the surface of substrate 76 is masked by mask layer 81, a portion 82 of which defines a large number of small exposed areas (the diffuser channels). Then an anisotropic etching step, using the mask layer 81, etches a number of very small micro channels 84 and a central hole 85 extending through substrate 76. This second mask layer 81 (including portions 82 thereof) is then stripped.

Figure 3D:
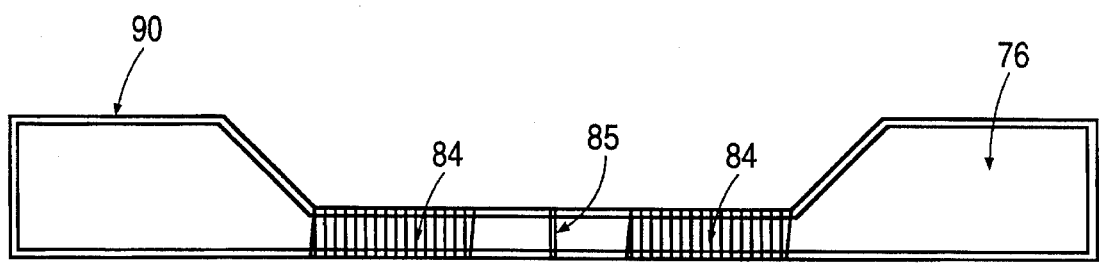

In one embodiment, the surface of the structure shown in FIG. 3d may then be coated by a metal layer 90. Each diffuser plate is then, as described above, scribed from the wafer. The diffuser plate is then assembled with the other components as shown in FIG. 2a. Fabrication of all other components is conventional.

The above description is illustrative and not limiting; further modifications will be apparent in light of this disclosure and are intended to be covered by the appended claims.

I claim:

1. A flame ionization detector comprising:

a base;

a tube attached to the base for carrying fuel and a fluid sample and being a bias electrode;

a diffuser attached to the base, a distal end of the tube extending through a surface of the diffuser;

a passage in the base for admitting an oxidant to the diffuser;

a collector electrode defining a central cavity and held spaced apart from the distal end of the tube;

whereby oxidant flowing through the passage in the base flows through the diffuser to the distal end of the central tube, and wherein the distal end of the tube is spaced apart less than 5 mm from the surface of the diffuser, thereby minimizing turbulence at the distal end of the tube.

2. The detector of claim 1, wherein the diffuser is a plate defining a plurality of diffuser channels.

3. The detector of claim 2, wherein the plate is formed of silicon.

4. The detector of claim 1, wherein the diffuser is a porous material.

5. The detector of claim 1, wherein the tube is of fused silica having a conductive layer formed on an outside wall of the tube, the conductive layer being the bias electrode.

6. The detector of claim 1, wherein an inner diameter of the tube is less than about 220 micrometers.

7. The detector of claim 1, further comprising an ignition element held in spaced relation from the distal end of the tube, the ignition element being a conductive element at least partly sheathed in an insulator.

8. The detector of claim 7, a tip of the ignition element being held less than about 8 mm from the distal end of the tube.

9. The detector of claim 1, further comprising an exhaust port located adjacent the collector;

wherein a total height of the flame ionization detector extending from the base to an outer end of the exhaust port is less than about 1.5 cm.

10. The detector of claim 1, wherein the diffuser defines a plurality of channels, and a diameter of each channel is less than about 2 micrometers.

11. The detector of claim 1, wherein the distal end of the tube is spaced apart from the surface of the diffuser by a distance less than about 2 mm.

12. The detector of claim 1, wherein the collector has an outer diameter less than about 7 mm, and a diameter of the collector central cavity is less than about 5 mm.

13. The detector of claim 1, wherein the passage extends in a direction perpendicular to an axis defined by the tube.

14. The detector of claim 2, wherein the diffuser plate has no diffuser holes in its central portion.

* * * * *